United States Patent [19]

Fourie et al.

[11] Patent Number: 4,578,520
[45] Date of Patent: Mar. 25, 1986

[54] PHLOROPHENONE DERIVATIVES, PROCESSES FOR PREPARING SUCH COMPOUNDS, USES AND PHARMACEUTICAL COMPOSITIONS OF PHLOROPHENONE COMPOUNDS

[75] Inventors: Theunis G. Fourie; Theodor G. Dekker; Friedrich O. Snyckers; Cornelis J. van der Schyf, all of Pretoria, South Africa

[73] Assignee: Noristan Limited, Pretoria, South Africa

[21] Appl. No.: 679,272

[22] Filed: Dec. 7, 1984

Related U.S. Application Data

[62] Division of Ser. No. 390,415, Jun. 21, 1982, Pat. No. 4,503,256.

[30] Foreign Application Priority Data

Jul. 2, 1981 [ZA] South Africa ............... 81/4480

[51] Int. Cl.$^4$ ............................................. C07C 45/68
[52] U.S. Cl. ..................................... 568/315; 568/316
[58] Field of Search ............... 568/315, 316, 766, 337, 568/796, 790, 789, 763

[56] References Cited

U.S. PATENT DOCUMENTS

| 2,681,371 | 6/1954 | Gaydasch et al. | 568/766 |
| 2,686,123 | 8/1954 | Campbell et al. | 568/337 |
| 2,898,374 | 8/1959 | Riedl | 568/315 |
| 3,467,715 | 9/1969 | Broadbent et al. | 568/337 |
| 3,846,498 | 11/1974 | Wild et al. | 568/315 |
| 3,853,956 | 12/1974 | Schmerling | 568/766 |
| 3,923,901 | 12/1975 | Battin et al. | 568/315 |
| 3,984,474 | 10/1976 | Tamai et al. | 568/393 |
| 3,985,783 | 10/1976 | Johnson et al. | 568/337 |
| 4,202,840 | 5/1980 | Gray et al. | 568/315 |
| 4,225,619 | 9/1980 | Brickl et al. | 568/337 |

FOREIGN PATENT DOCUMENTS 2738588 3/1978 Fed. Rep. of Germany ...... 568/315

OTHER PUBLICATIONS

Mil' Kanovitskaya et al., Chem. Abst, vol. 54, #20948c.

Primary Examiner—James H. Reamer
Attorney, Agent, or Firm—Ladas & Parry

[57] ABSTRACT

Novel compounds of general formula I

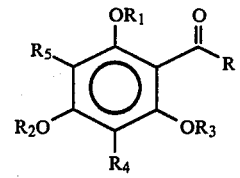

wherein R is a branched or unbranched alkyl, cycloalkyl, or aralkyl group, which group optionally contains or is substituted by a halogen or oxygen function, the oxygen function optionally being in the form of an alcohol or ether moiety;

$R_1$, $R_2$, and $R_3$, which may be the same or different, is hydrogen, an alkyl, acyl, or benzoyl group, which group optionally contains or is substituted by a halogen or oxygen function;

$R_4$ is hydrogen, an alkyl, alkenyl preferably being an allyl or prenyl group, or aralkyl group which group optionally contains or is substituted by an alkyl, aryl, halogen or oxygen function;

$R_5$ is hydrogen, an alkyl, aralkyl, acyl, or aryl group, which group optionally contains or is substituted by an alkyl, aryl, halogen, or oxygen function; except that $R_4$ and $R_5$ are not both hydrogen;

and except for the compounds when $R_5$ is hydrogen and R is methyl, i-propyl, branched butyl, methoxy methyl, 2-phenylethyl, or 2-phenylethylene;

chromans and dihydrobenzofurans derived from these compounds;

pharmaceutically acceptable salts, and metabolites and metabolic precursors of these compounds;

processes for preparing the aforementioned types of compounds; use of the aforementioned types of compounds as antibacterial and/or antimycotic agents; and pharmaceutical compositions of such compounds.

18 Claims, No Drawings

PHLOROPHENONE DERIVATIVES, PROCESSES FOR PREPARING SUCH COMPOUNDS, USES AND PHARMACEUTICAL COMPOSITIONS OF PHLOROPHENONE COMPOUNDS

This is a divisional of co-pending application Ser. No. 390,415, filed on June 21, 1982, now U.S. Pat. No. 4,503,256.

This invention relates to phlorophenone derivatives, processes for preparing such compounds, uses and pharmaceutical compositions of phlorophenone compounds. More particularly, this invention relates to various phlorophenone and related chroman and dihydrobenzofuran compounds, processes for preparing such compounds; antibacterial and antimycotic uses, and pharmaceutical compositions of such-like compounds.

BACKGROUND OF THE INVENTION

W. Riedl in Chemische Berichte, 85, 692 (1952) described the synthesis of humulon and lupulone compounds which had been known to exist in nature and which had further been known to possess certain antibiotic properties. In this publication he reported the synthesis of humulon by diprenylation of the disodium salt of phlorisovalerophenone yielding as a byproduct (9%—see compound XV on page 701) 3-prenyl phlorisovalerophenone In this publication, W. Riedl also reported that, during the synthesis of 4-desoxy humulon, a byproduct was obtained which was speculated to comprise a chroman or benzodipyran. However, the structure hereof was not further examined nor reported. although this byproduct exhibited certain antibacterial activity.

F. Bohlman and various co-workers in a number of publications have reported the extraction of various compounds (mainly in the form of mixtures) from certain Helicrysum plant species, which compounds were postulated to have the 3-alkenyl phlorophenone structure. Certain related chromans were also extracted or prepared from compounds extracted from the plant material. However, as far as the inventors of the present invention are aware, no antimicrobial properties of these compounds have been reported.

V. K. Ahluwalia and various co-workers in Synthesis, 526 and 527, (1981) reported the synthesis of chromans and dichromans, both classes of compounds being derived from the corresponding phlorophenone compound. Although the aforementioned types of compounds are known to have certain physiological activities, for example including antioxidant, tranquillizing, and antidepressant properties and properties relating to fertility, it appears as if no antimicrobial properties of these compounds have been reported (see reference number 2 in the first-mentioned paper by Ahluwalia et al).

Other workers are known to have prepared phlorophenones, chromans, and dihydrobenzofurans, for example, A. Robertson and T. S. Subramanian, J. Chem. Soc., 286 (1937) and 1545 (1937); R. A. Finnegan et al, Tetrahedron, 13, 11 (1959); E. D. Burling et al, Tetrahedron, 21, 2653 (1965); P. W. Austin et al, Tetrahedron, 24, 3247 (1968); R. Hänsel et al, Phytochem, 19, 639 (1980). Likewise, however, as far as the inventors of the present invention are aware, no antimicrobial activity or properties of these compounds have been reported.

It has long been known that phenols and chlorinated phenols exhibit bactericidal action. Phenol itself, the simplest member of the series was already introduced as an antiseptic during the nineteenth century. It has been shown that the more highly substituted phenol derivatives are more selective in their action than the simpler phenols, and some of the more highly substituted phenol derivatives also exhibit antifungal activity. The more selective phenols are used mostly for skin disinfections, whilst the less refined members are used as general disinfectants, for instance in the disinfection of floors, drains, and stables for example. Phenols are also used as preservatives in pharmaceutical preparations.

OBJECTS OF THE INVENTION

This invention has an object novel phlorophenone compounds and related chromans and dihydrobenzofurans; novel processes for preparing phlorophenone compounds and related chromans and dihydrobenzofurans; novel antibacterial and/or antimycotic uses of such-like compounds; and pharmaceutical compositions of these types of compounds.

SUMMARY OF THE INVENTION

According to one aspect of the present invention there are provided novel compounds of general formula I

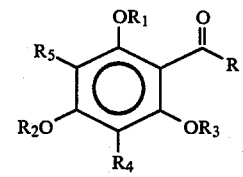

wherein R is a branched or unbranched alkyl, cycloalkyl, or aralkyl group, which group may optionally contain or be substituted by a halogen or oxygen function, the oxygen function preferably being in the form of an alcohol or ether moiety; $R_1$, $R_2$, and $R_3$, which may be the same or different, is hydrogen, an alkyl, acyl, or benzoyl group, which group may optionally contain or be substituted by a halogen or oxygen function;

$R_4$ is hydrogen, an alkyl, alkenyl (preferably such as an allyl or prenyl) or aralkyl group, which group may optionally contain or be substituted by an alkyl, aryl, halogen or oxygen function; $R_5$ is hydrogen, an alkyl, aralkyl, acryl, or aryl group, which group may optionally contain or be substituted by an alkyl, aryl, halogen, or oxygen function;

except that $R_4$ and $R_5$ are not both hydrogen; and except for the compounds when $R_5$ is hydrogen and R is methyl, i-propyl, branched butyl, methoxy methyl, 2-phenylethyl, or 2-phenylethylene; pharmaceutically acceptable salts thereof, and metabolites and metabolic precursors of the aforegoing.

It is to be understood that the novel phlorophenone compounds, and related chromans and dihydrobenzofurans according to the invention are included within the scope of general formula I. However, for purposes of further discussion, these three types of compounds will be discussed hereunder with reference to further general formulae in order to defined these novel compounds more clearly.

Therefore also according to the invention there are provided novel phlorophenone compounds of general formula II

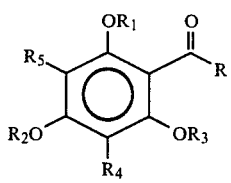

wherein R, $R_1$, $R_2$, $R_3$, $R_4$, and $R_5$ are as defined for general formula I, and wherein $R_1$, $R_2$, and/or $R_3$ is/are not directly bonded to any group defined by $R_4$ and/or $R_5$. In other words, compounds of general formula II are to be understood to exclude compounds having a cyclic moiety associated with substituents $R_1$, $R_2$, and/or $R_3$.

In the case that in general formula II the substituent group for $R_4$ is directly bonded to either $R_2$ or $R_3$ respectively, there are obtained
(i) chromans of general formula III as defined hereunder:

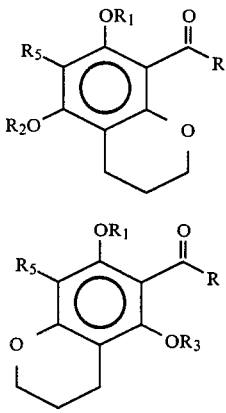

wherein R, $R_1$, and/or $R_2$ in the case of general formula IIIa, and $R_3$ in the case of general formula IIIb, and $R_5$ are as hereinbefore defined for general formula II;

and wherein the O-containing ring is optionally unsaturated and/or optionally substituted by one or more alkyl, aralkyl, or aryl group(s), which group(s) optionally contain(s) or is/are substituted by an alkyl, halogen or oxygen function; and
(ii) dihydrobenzofurans of general formula IV

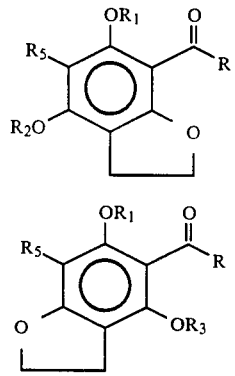

wherein R, $R_1$, $R_2$ in the case of general formula IVa and $R_3$ in the case of general formula IVb, and $R_5$ are as hereinbefore defined for general formula II;

and wherein the O-containing ring is optionally unsaturated and/or optionally substituted by one or more alkyl, aralkyl, or aryl group(s), which group(s) optionally contain(s) or is/are substituted by an alkyl, halogen or oxygen function.

Generally preferred compounds of general formula II include compounds wherein $R_1$, $R_2$, and $R_3$ are hydrogen, $R_4$ is an allyl, prenyl, or benzyl group, and $R_5$ is hydrogen;

or compounds wherein $R_1$, $R_2$, $R_3$, and $R_4$ are hydrogen, and $R_5$ is an acyl group.

Generally preferred compounds of general formula III are the compounds having structure IIIa wherein $R_1$, $R_2$, and $R_5$ are hydrogen, and the α carbon atom in the O-containing ring is mono or dialkylated, more specifically mono or dimethylated.

Preferred compounds of general formula IV include compounds wherein $R_1$, $R_2$, or $R_3$, and $R_5$ are hydrogen.

Particularly preferred compounds of the above general formulae are listed in Table 1 hereunder.

TABLE 1

| GENERAL FORMULA | R | $R_1$ | $R_2$ | $R_3$ | $R_4$ | $R_5$ | SUBSTITUENTS IN O-CONTAINING RING POSITION(S) | SUBSTITUENT(S) | COMP. NUMBER |
|---|---|---|---|---|---|---|---|---|---|
| II | —CH$_2$CH$_2$CH$_3$ | H | H | H | H | —C(=O)CH$_2$CH$_2$CH$_3$ | | | 1 |
| II | —CH$_2$CH$_3$ | H | H | H | —CH$_2$CH:C(CH$_3$)$_2$ | H | | | 2 |
| II | —CH$_2$CH$_2$CH$_3$ | H | H | H | —CH$_2$CH:C(CH$_3$)$_2$ | H | | | 3 |
| II | —CH$_2$CH$_2$CH$_2$CH$_3$ | H | H | H | —CH$_2$CH:C(CH$_3$)$_2$ | H | | | 4 |
| II | —CH$_2$CH$_2$CH$_2$CH$_2$CH$_3$ | H | H | H | —CH$_2$CH:C(CH$_3$)$_2$ | H | | | 5 |
| II | —CH$_2$C$_6$H$_5$ | H | H | H | —CH$_2$CH:C(CH$_3$)$_2$ | H | | | 6 |
| II | —CH$_2$CH$_2$CH(CH$_3$)$_2$ | H | H | H | —CH$_2$CH:C(CH$_3$)$_2$ | H | | | 7 |
| II | —CHCH$_2$CH$_2$CH$_2$CH$_2$— | H | H | H | —CH$_2$CH:C(CH$_3$)$_2$ | H | | | 8 |
| II | —CHCH$_2$CH$_2$CH$_2$CH$_2$— | H | H | H | —CH$_2$CH:C(CH$_3$)$_2$ | H | | | 9 |
| II | —CH$_2$(CH$_2$)$_6$CH$_3$ | H | H | H | —CH$_2$CH:C(CH$_3$)$_2$ | H | | | 10 |
| II | —CH$_2$(CH$_2$)$_5$CH$_3$ | H | H | H | —CH$_2$CH:C(CH$_3$)$_2$ | H | | | 11 |
| II | —CH$_2$(CH$_2$)$_4$CH$_3$ | H | H | H | —CH$_2$CH:C(CH$_3$)$_2$ | H | | | 12 |
| II | —CH$_2$C$_6$H$_4$Cl(p) | H | H | H | —CH$_2$CH:C(CH$_3$)$_2$ | H | | | 14 |
| II | —CH$_2$CH$_3$ | H | H | H | —CH$_2$CH:CH$_2$ | H | | | 15 |
| II | —CH$_2$CH$_2$CH$_3$ | H | H | H | —CH$_2$CH:CH$_2$ | H | | | 16 |
| II | —CH$_2$CH$_2$CH$_2$CH$_3$ | H | H | H | —CH$_2$CH:CH$_2$ | H | | | 17 |
| II | —CH$_2$(CH$_2$)$_3$CH$_3$ | H | H | H | —CH$_2$CH:CH$_2$ | H | | | 18 |
| II | —CH$_2$CH$_2$CH(CH$_3$)$_2$ | H | H | H | —CH$_2$CH:CH$_2$ | H | | | 19 |
| II | —CHCH$_2$CH$_2$CH$_2$CH$_2$— | H | H | H | —CH$_2$CH:CH$_2$ | H | | | 20 |
| II | —CH$_2$CH$_2$CH$_3$ | H | H | H | —CH$_2$CH:CH$_2$ | —C(=O)CH$_2$CH$_2$CH$_3$ | | | 21 |
| II | —CH$_2$CH$_2$OCH$_2$CH$_3$ | H | H | H | —CH$_2$CH:CH$_2$ | H | | | 22 |
| II | —CH$_2$C$_6$H$_4$Cl(p) | H | H | H | —CH$_2$CH:CH$_2$ | H | | | 23 |
| II | —CH$_2$CH$_2$CH$_3$ | H | H | H | —CH$_2$C$_6$H$_5$ | H | | | 24 |
| II | —CH$_2$CH$_2$CH(CH$_3$)$_2$ | H | H | H | —CH$_2$C$_6$H$_5$ | H | | | 25 |
| II | —CHCH$_2$CH$_2$CH$_2$CH$_2$— | H | H | H | —CH$_2$C$_6$H$_5$ | H | | | 26 |
| II | —CH$_2$(CH$_2$)$_6$CH$_3$ | H | H | H | —CH$_2$C$_6$H$_5$ | H | | | 27 |

TABLE 1-continued

| GENERAL FORMULA | R | R$_1$ | R$_2$ | R$_3$ | R$_4$ | R$_5$ | SUBSTITUENTS IN O—CONTAINING RING POSITION(S) | SUBSTITUENTS IN O—CONTAINING RING SUBSTITUENT(S) | COMP. NUMBER |
|---|---|---|---|---|---|---|---|---|---|
| II | —CH$_2$CH$_2$CH(CH$_3$)$_2$ | —C(=O)—C$_6$H$_4$Br(p) | —C(=O)—C$_6$H$_4$Br(p) | H | —CH$_2$CH:C(CH$_3$)$_2$ | H | | | 28 |
| II | —CH$_2$CH$_2$CH(CH$_3$)$_2$ | CH$_3$ | CH$_3$ | H | —CH$_2$CH:C(CH$_3$)$_2$ | H | | | 29 |
| IIIa | —CH$_2$CH$_2$CH$_3$ | H | H | | | H | 2,2 | CH$_3$, CH$_3$ | 30 |
| IIIa | —CH$_2$CH$_2$CH(CH$_3$)$_2$ | H | H | | | H | 2,2 | CH$_3$, CH$_3$ | 31 |
| IIIa | —CH$_2$(CH$_2$)$_6$CH$_3$ | H | H | | | H | 2,2 | CH$_3$, CH$_3$ | 32 |
| IIIb | —CH$_2$CH$_2$CH(CH$_3$)$_2$ | H | | H | | H | 2,2 | CH$_3$, CH$_3$ | 33 |
| IIIb | —CH$_2$(CH$_2$)$_6$CH$_3$ | H | | H | | H | 2,2 | CH$_3$, CH$_3$ | 34 |
| IVa or IVb | —CH$_2$CH$_2$CH$_3$ | H | R$_2$ or R$_3$ = H | | | H | 2 | CH$_3$ | 35 |
| IIIa | —CH$_2$CH$_2$CH$_3$ | H | H | | | —C(=O)CH$_2$CH$_2$CH$_3$ | 2,2 | CH$_3$, CH$_3$ | 36 |
| IVa | —CH$_2$CH$_2$CH$_3$ | H | H | | | —C(=O)CH$_2$CH$_2$CH$_3$ | 2 | CH$_3$ | 37 |

Most preferred compounds of the above general formulae are listed hereunder. The number appearing after each compound is the compound reference number referred to in the last column in Table 1 as Compound (comp.) number. These compound numbers are also used in the examples hereunder to assist in clearly defining the various compounds according to this invention.

2,4-Dibutyrylphloroglucinol (1)
2-Caproyl-4-(3-methylbuten-2-yl)phloroglucinol. (5)
2-Isocaproyl-4-(3-methylbuten-2-yl)phloroglucinol. (7)
2-Hexahydrobenzoyl-4-(3-methylbuten-2-yl)=phloroglucinol (8)
2-(2-Cyclopentyl-1-oxo)-4-(3-methylbuten-2-yl)=phloroglucinol. (9)
2-Isocaproyl-4-(propen-2-yl)phloroglucinol. (19)
2-Isocaproyl-4-benzylphloroglucinol. (25)
2-Nonanoyl-4-benzylphloroglucinol. (27)
5,7-Dihydroxy-2,2-dimethyl-8-isocaproylchroman. (31)
5,7-Dihydroxy-2,2-dimethyl-8-nonanoyl chroman. (32)
7-Butyryl-4,6-dihydroxy-2-methyl-2,3-dihydrobenzofuran
5-Butyryl-4,6-dihydroxy-2-methyl-2,3-dihydrobenzofuran. (35)

According to another aspect of the invention there are provided novel processes for preparing compounds of general formula I as hereinbefore defined including the excepted compounds, one process including the step of treating a parent phlorophenone compound with an appropriate organic halide, preferably an organic chloride compound, in the presence of a catalyst and a base. A preferred catalyst is cuprous chloride and a preferred base is for example sodium carbonate. This reaction is preferably carried out in a two phase system by dissolving or suspending the phlorophenone and cuprous chloride in ether or any suitable hydrophobic solvent, adding saturated sodium carbonate, and finally adding the organic chloride to the well stirred two phase system. Alternatively the process includes treatment of the sodium salt of the parent phlorophenone in an aprotic medium, such as benzene, with an appropriate halide, preferably the bromide compound.

Compounds of general formula II wherein $R_5$ is hydrogen can be prepared as outlined above; whilst compounds of general formula II wherein $R_5$ is an acyl group can be prepared
 (i) by acylation of a phlorophenone compound, for example with an appropriate acid chloride in the presence of aluminium chloride; or alternatively,
 (ii) for preparing compounds wherein $R_5$ is butyryl (see for example compound 1), an appropriate phlorophenone compound can be reacted with methanesulphonic acid and acrylic acid in the presence of phosphorous pentoxide.

The invention also provides a process for preparing compounds of the general formula III, one such preferred process being treatment of a phlorophenone derivative wherein $R_4$ is prenyl with an appropriate acid, for example with trifluoro acetic acid in benzene, yielding the corresponding chroman derivatives IIIa and/or IIIb.

Reaction of 3-prenyl phloroglucinol (which can be prepared by treatment of phloroglucinol with prenyl chloride in the presence of a catalyst, such as cuprous chloride, and a base such as sodium carbonate, in a two phase system according to the general procedure as described above for the preparation of the prenyl compounds of general formula II) with an acid chloride in the presence of aluminium chloride in a suitable solvent such as carbon disulphide and nitrobenzene, leads to the formation of a mixture of products from which the corresponding chroman compound wherein $R_5$ is an acyl group can be isolated, for example by means of chromatography, or any other known method.

Reaction of a 3-allyl phloroglucinol, which can be prepared according to the method outlined immediately above from phloroglucinol and allyl chloride, with acid chloride in the presence of aluminium chloride in a suitable solvent such as carbon disulphide and nitrobenzene, leads to formation of compounds of general formula IV, i.e. dihydrobenzofuran in which $R_5$ is hydrogen or an acyl group.

It will be readily apparent to a person skilled in the art that the ether derivatives of compounds of the general formula I are prepared according to standard procedures applied for the etherification of a phenol, for example by reaction with dimethyl sulphate under basic conditions. Likewise, acetylation of phenolic groups of compounds of general formula I is accomplished according to standard procedures described for phenols, for example by treatment with an appropriate acid chloride in dry benzene, or by treatment with an appropriate anhydride in a basic medium.

Treatment of chromans and dihydrobenzofurans, being compounds of general formulae III and IV respectively, with 2, 3-dichloro-5,6-dicyanobenzoquinone (DDQ) in a dry aprotic solvent, such as benzene, leads to the formation of the corresponding chromenes and benzofurans, a conversion that usually proceeds at a high yield.

The invention naturally extends to compounds whenever prepared according to any of the novel processes of the invention.

Compounds of general formula I and the related chromans and dihydrobenzofurans, including the excepted compounds, have generally shown useful antimicrobial activity, more particularly antibacterial and/or antimycotic properties. Accordingly, the invention extends to use of such compounds for these purposes, for example for treating humans or animals for bacterial and/or mycotic infections, or preserving food, beverages, natural proucts, and as a general disinfectant.

According to a further aspect of the invention there are provided pharmaceutical compositions comprising as an active ingredient, a pharmaceutically acceptable amount of at least one pharmacologically acceptable compound of general formula I including the excepted compounds, either alone or in admixture with a suitable diluent or adjuvant. Preliminary investigations into the formation of bacterial/fungal resistance to certain of these compounds indicate no significant formation of resistance by the bacteria/fungi tested. These investigations indicate that such resistance is at least lower than against nitrofurantoin which was used as a reference compound.

DETAILED DESCRIPTION OF THE INVENTION

The invention will now be described in greater detail hereunder by way of the following non-limiting examples.

EXAMPLE 1

The entire plant material of *Helichrysum caespititium* was air dried, crushed and extracted consecutively with benzene, ethyl acetate and methanol. These extractions were carried out at room temperature for a period of 48 hours. The extracts were separately stripped to dryness under reduced pressure at temperatures not exceeding 50° C. 2-Isocaproyl-4-(3-methylbuten-2-yl)phloroglucinol was isolated from each of the three extraction residues by means of chromatography preferably on silica gel (open column chromatography, preparative HPLC chromatography or preparative TLC) using preferably mixtures of benzene and ethyl acetate or petroleum ether and ethyl acetate for eluation. The 2-isocaproyl-4-(3-methylbuten-2-yl)phloroglucinol (7) was obtained as straw coloured crystals, m.p. 132°–133° C., from benzene.

IR spectrum (KBr-disc): 3420 (br, st), 2970 (m), 2930 (m), 2880 (w), 1630 (sh), 1610 (st), 1595 (st), 1560 (m), 1440 (st), 1385 (w), 1365 (w), 1280 (m), 1225 (st), 1215 (sh), 1145 (m), 1120 (w), 1075 (m) and 820 (m) cm$^{-1}$.

$^1$H NMR spectrum (CDCl$_3$+CD$_3$OD): δ13.33 (s; 1H); 5.90 (s; 1H); 5.25 (br,t; J≃7 Hz; 1H); 3.4–2.9 (c; four prominant signals at δ3.33; 3.22; 3.08 ad 2.97; 4H); 1.83–1.43 (c; with sharp signals at δ1.78 and 1.70; 9H) and 0.93 (d; J167 5 Hz; 6H).

$^{13}$C NMR spectrum (DMSO-d$_6$): δ205.6; 163.4; 162.1; 159.8; 129.3; 123.5; 105.9; 103.6; 94.2; 41.1; 33.7; 27.4; 25.4; 22.3; 20.9 and 17.6.

EXAMPLE 2

Phlorisocaprophenone (4.48 g) was dissolved in ether (30 ml). To this solution was added cuprous chloride (100 mg), saturated aqueous solution (30 ml) of sodium carbonate and prenyl chloride (2.1 g). The mixture was stirred or shaken vigorously for 12 hours. The ether phase was separated and the water phase was extracted twice with ether (25 ml). The ether solutions were combined, washed with water, dried over sodium sulphate and stripped to dryness under reduced pressure at room temperature. 2-Isocaproyl-4-(3-methylbuten-2-yl)phloroglucinol (7) was isolated from the residue by means of chromatography on silica gel (open column chromatography on preparative HPLC) using preferably mixtures of benzene and ethyl acetate or petroleum ether and ethyl acetate for eluation. Recrystallization from benzene afforded straw coloured crystals, identical to the same prepared in Example 1.

EXAMPLE 3

To a solution of phlorisocaprophenone (5 g) in dry ether (50 ml) was first added dry benzene (100 ml) and then a solution of sodium (0.52 g) in absolute ethanol (30 ml). The mixture was concentrated to about 80 ml, whereupon the sodium salt of phlorisocaprophenone separated as a fine yellowish precipitate. To this well stirred suspension was added a solution of prenyl bromide (3.3 g) in benzene (10 ml) over a period of 15 minutes. The mixture was refluxed for a period of 3 hours and filtered to remove sodium bromide. The filtrate was evaporated to dryness and 2-isocaproyl-4-(3-methylbuten-2-yl)phloroglucinol (7) was isolated from the residue by chromatography according to the procedure described in Example 2. The 2-isocaproyl-4-(3-methylbuten-2-yl)phloroglucinol prepared according to this method was identical to the compound obtained in Examples 1 and 2.

EXAMPLES 4 TO 14

The compounds described in Examples 4 to 14 vary only in the phenone moiety and were prepared by starting with the appropriate phlorophenone, purified and recrystallized according to both the procedures described in Example 2 and Example 3. The quantity of phlorophenone substrate used in each of the preparations was adjusted according to its molecular mass.

EXAMPLE 4

2-Butyryl-4-(3-methylbuten-2-yl)phloroglucinol (3) from phlorobutyrophenone.

IR spectrum (KBr-disc): 3430 (st), 3360 (br, st), 2980 (w), 2950 (w), 2930 (w), 1640 (sh), 1625 (st), 1610 (sh), 1580 (m), 1460 (st), 1400 (m), 1380 (m), 1325 (m), 1300 (w), 1230 (st), 1160 (m), 1120 (w), 1090 (st), 1060 (w) and 835 (m) cm$^{-1}$.

$^1$H NMR spectrum (CDCl$_3$+CD$_3$OD): δ5.86 (s; 1H); 5.18 (br,t; J≃7 Hz; 1H); 3.40–2.90 (c; with prominent signals at δ3.28; 3.15; 3.05 and 2.90; 4H); 1.90–1.50 (c; with sharp signals at δ1.75 and 1.65; 8H) and 0.97 (t; J≃7 Hz; 3H).

$^{13}$C NMR spectrum (DMSO-d$_6$): ≃163.4; 159.8; 129.4; 123.5; 105.9; 103.7; 94.2; 45.1; 25.4; 21.0; 17.9; 17.6 and 13.8 and one signal below 200.

EXAMPLE 5

2-Nonanoyl-4-(3-methylbuten-2-yl)phloroglucinol (10) from phlorononaphenone.

IR spectrum (KBr-disc): 3420 (br, st), 2930 (m), 2870 (m), 1625 (st), 1610 (st), 1580 (m), 1510 (w), 1475 (w), 1445 (st), 1395 (w), 1375 (w), 1280 (m), 1240 (st), 1210 (m), 1160 (m), 1085 (st) and 840 (m) cm$^{-1}$.

$^{13}$C NMR spectrum (DMSO-d$_6$): δ205.3; 163.4; 162.1; 159.8; 129.4; 123.5; 105.9; 103.6; 94.1; 43.1; 31.3; 29.0 (2×C); 28.6; 25.4; 24.6; 22.1; 21.0; 17.6 and 13.9.

EXAMPLE 6

2-Phenylacetyl-4-(3-methylbuten-2-yl)phloroglucinol (6) from phlorophenylacetophenone. IR spectrum (KBr-disc): 3420 (st), 3340 (br,m), 2980 (w), 2920 (w), 1635 (st), 1625 (st), 1595 (m), 1560 (m), 1435 (br, st), 1395 (w), 1350 (m), 1240 (st), 1210 (m), 1180 (w), 1150 (m), 1085 (st), 830 (m), 735 (m) and 710 (w) cm$^{-1}$.

$^1$H NMR spectrum (CDCl$_3$+CD$_3$OD): δ 7.23 (s; 5H); 5.88 (s; 1H); 5.25 (br, t; J≃7 Hz; 1H); 4.45 (s; 2H); 3.31 (d; J≃7 Hz; 2H); 1.82 (s; 3H) and 1.73 (s; 3H).

$^{13}$C NMR spectrum (CDCl$_3$+CD$_3$OD): δ 203.3; 163.2; 162.1; 160.3; 136.1; 132.8; 129.9 (2×C); 128.3 (2×C); 126.5; 122.7; 106.8; 104.8; 94.5; 49.9; 25.7; 21.5 and 17.8.

EXAMPLE 7

2-Hexahydrobenzoyl-4-(3-methylbuten-2-yl)phloroglucinol (8) rom phlorohexahydrobenzophenone.

IR spectrum (KBr-disc): 3490 (br, m), 2920 (m), 2860 (w), 1625 (st), 1600 (sh), 1540 (w), 1510 (w), 1445 (st), 1375 (m), 1335 (w), 1315 (w), 1265 (st), 1255 (sh), 1220 (st), 1180 (m), 1150 (m), 1130 (m), 1080 (m), 1070 (sh), 1050 (sh), 1000 (w) and 825 (w) cm$^{-1}$.

$^1$H NMR spectrum (DMSO-d$_6$): δ 14.02 (s; 1H); 5.90 (s; 1H); 5.05 (br, t; J≃7 Hz; 1H); 3.28 (c; 1H); 3.03 (br, d; J≃7 Hz); 2H) and 1.95–1.05 (c with sharp signals at 1.66 and 1.58; 16H).

$^{13}$C NMR spectrum (DMSO-d$_6$): δ 208.5; 163.8; 162.0; 159.5; 129.3; 123.5; 106.0; 102.9; 94.3; 48.5; 29.2 (2×C); 25.8 (3×C); 25.4; 21.0 and 17.6.

EXAMPLE 8

2-Propionyl-4-(3-methylbuten-2-yl)phloroglucinol (2) from phloropropiophenone.

IR spectrum (KBr-disc): 3400 (br, st), 2990 (w), 2940 (w), 1620 (br, st), 1585 (m), 1525 (w), 1510 (w), 1465

(sh), 1450 (st), 1435 (sh), 1400 (w), 1380 (m), 1370 (m), 1255 (st), 1240 (st), 1160 (m), 1100 (sh), 1090 (m), 1055 (w), 1000 (w), 900 (br, w) and 840 (m) cm$^{-1}$.

$^{13}$C NMR spectrum (DMSO-d$_6$): δ 205.7; 163.2; 162.1; 159.9; 129.4; 123.5; 105.8; 103.5; 94.1; 36.4; 25.4; 21.0; 17.6 and 8.9.

EXAMPLE 9

2-Valeryl-4-(3-methylbuten-2-yl)phloroglucinol (4) from phlorovalerophenone.

IR spectrum (KBr-disc): 3430 (st), 3330 (br, m), 2960 (w), 2930 (br, w), 2880 (w), 1640 (sh), 1630 (st), 1605 (m), 1565 (m), 1530 (w), 1510 (w), 1465 (sh), 1450 (st), 1435 (sh), 1395 (m), 1385 (sh), 1360 (w), 1290 (m), 1240 (st), 1225 (m), 1185 (w), 1160 (m), 1120 (w), 1090 (st), 1060 (w), 1020 (w), 905 (w) and 835 (m) cm$^{-1}$.

$^{13}$C NMR spectrum (DMSO-d$_6$): δ 205.3; 163.4; 162.1; 159.8; 129.4; 124.5; 105.9; 103.6; 94.2; 42.8; 26.8; 25.4; 22.1; 21.0; 17.6 and 13.8.

EXAMPLE 10

2-Caproyl-4-(3-methylbuten-2-yl)phloroglucinol (5) from phlorocaprophenone.

IR spectrum (KBr-disc): 3410 (br, st), 2970 (w), 2930 (br, m), 2880 (w), 1635 (sh), 1625 (st), 1610 (m), 1580 (m), 1525 (w), 1510 (w), 1450 (st), 1400 (w), 1380 (w), 1335 (m), 1300 (w), 1275 (m), 1250 (sh), 1235 (w), 1215 (st), 1195 (w), 1160 (m), 1125 (br, w), 1085 (st) and 835 (m) cm$^{-1}$.

$^{13}$C NMR spectrum (DMSO-d$_6$): δ 205.3; 163.4; 162.1; 159.8; 129.4; 123.5; 105.9; 103.7; 94.2; 43.1; 31.2; 25.4; 24.3; 22.0; 21.0; 17.6 and 13.8.

EXAMPLE 11

2-Octanoyl-4-(3-methylbuten-2-yl)phloroglucinol (11) from phloroctanophenone.

IR spectrum (KBr disc): 3420 (br, st), 2960 (w), 2920 (m), 2850 (w), 1650 (st), 1630 (st), 1610 (m), 1590 (m), 1555 (w), 1530 (w), 1520 (w), 1470 (sh), 1450 (st), 1400 (m), 1380 (br, m), 1290 (m), 1255 (st), 1245 (sh), 1210 (m), 1195 (w), 1155 (m), 1130 (w), 1080 (st), 905 (br, w) and 830 (m) cm$^{-1}$.

$^{13}$C NMR spectrum (DMSO-d$_6$): δ 205.3; 163.4; 162.1; 159.8; 129.3; 123.5; 105.9; 103.7; 94.2; 43.1; 31.2; 28.9; 28.6; 25.4; 24.6; 22.1; 21.0; 17.6 and 13.8.

EXAMPLE 12

2-(2-Cyclopentyl-1-oxo)-4-(3-methylbuten-2-yl)phloroglucinol (9) from 2-(2-cyclopentyl-1-oxo)phloroglucinol.

IR spectrum (KBr-disc): 3420 (br, st), 2960 (m), 2920 (br, w), 2860 (w), 1645 (sh), 1635 (st), 1615 (st), 1585 (w), 1570 (w), 1520 (br, w), 1465 (sh), 1460 (st), 1450 (sh), 1380 (br, m), 1310 (br, w), 1290 (br, w), 1245 (st), 1180 (w), 1150 (m), 1110 (w), 1080 (st) and 830 (m) cm$^{-1}$.

Mass spectrum: m/e 290 (M$^+$), 235, 221, 207, 191, 165 (100%), 153, 139, 97 and 69.

EXAMPLE 13

2-Heptanoyl-4-(3-methylbuten-2-yl)phloroglucinol (12) from phloroheptanophenone.

IR spectrum (KBr-disc): 3420 (br, st), 2960 (w), 2940 (sh), 2920 (m), 2860 (sh), 2850 (w), 1660 (sh), 1645 (m), 1635 (st), 1615 (m), 1590 (m), 1530 (w), 1520 (w), 1455 (st), 1400 (m), 1380 (m), 1355 (w), 1310 (sh), 1300 (m), 1265 (m), 1250 (m), 1230 (m), 1210 (st), 1195 (w), 1155 (m), 1130 (w), 1085 (st), 1070 (sh), 905 (br, w) and 830 (m) cm$^{-1}$.

$^{13}$C NMR spectrum (DMSO-d$_6$): δ 205.3; 163.4; 162.1; 159.8; 129.3; 123.5; 105.9; 103.7; 94.2; 43.1; 31.2; 28.6; 25.4; 24.6; 22.0; 21.0; 17.6 and 13.8.

EXAMPLE 14

2-(4-Chlorophenyl)acetyl-4-β-methylbuten-2-yl)phloroglucinol (14) from phloro-p-chlorophenylacetophenone.

IR spectrum (KBr-disc): 3420 (st), 3320 (br, m), 2970 (w), 2910 (w), 1650 (sh), 1630 (m), 1620 (st), 1600 (m), 1555 (m), 1520 (w), 1505 (w), 1490 (w), 1455 (sh), 1440 (st), 1430 (m), 1395 (m), 1375 (w), 1340 (m), 1310 (w), 1280 (w), 1250 (sh), 1230 (st), 1200 (m), 1180 (w), 1145 (m), 1095 (w), 1080 (st), 1050 (w), 1025 (w), 875 (m), 830 (w), 815 (m) and 780 (w) cm$^{-1}$.

$^{13}$C NMR spectrum (DMSO-d$_6$): δ 201.8; 163.4; 162.6; 159.9; 135.1; 131.5 (2×C); 131.0; 129.5; 127.9 (2×C); 123.3; 106.0; 103.5; 94.2; 48.2; 25.4; 20.9 and 17.5.

EXAMPLES 15 TO 22

The compounds described in Examples 15 to 22 were prepared and purified according to the procedure described in Example 2 by reacting the appropriate phlorophenone with slightly more than one molar equivalent allyl chloride instead of prenyl chloride.

EXAMPLE 15

2-Isocaproyl-4-(propen-2-yl)phloroglucinol (19) from phlorisocaprophenone.

IR spectrum (KBr-disc): 3440 (st), 3140 (br, m), 2950 (m), 2920 (sh), 2870 (w), 1630 (m), 1600 (st), 1565 (m), 1495 (w), 1445 (st), 1425 (m), 1365 (w), 1315 (m), 1295 (st), 1275 (st), 1250 (m), 1225 (st), 1195 (m), 1150 (w), 1125 (st), 1100 (w), 1070 (st), 915 (m), 860 (w) and 805 (m) cm$^{-1}$.

$^1$H NMR spectrum (CDCl$_3$+CD$_3$OD): δ 13.35 (s; 1H); 6.30–5.60 (c; with sharp signal at δ 5.80; 2H); 5.20–4.80 (c; 2H); 3.45–2.90 (c; with prominent signals at δ 3.33; 3.23; 3.17; 3.05 and 2.92; 4H); 1.80–1.30 (c; with prominent signals at δ 1.65; 1.55 and 1.45; 3H) and 0.91 (d; J≃5 Hz; 6H).

$^{13}$C NMR spectrum (DMSO-d$_6$): δ 205.6; 163.6; 162.3; 160.1; 136.8; 113.8; 104.1; 103.6; 94.2; 41.2; 33.7; 27.5; 26.1 and 22.3 (2×C).

EXAMPLE 16

2-Butyryl-4-(propen-2-yl)phloroglucinol (16) from phlorobutyrophenone.

IR spectrum (KBr-disc): 3460 (br, st), 3360 (br, st), 2980 (w), 2960 (w), 2900 (w), 1625 (st), 1610 (sh), 1570 (m), 1530 (w), 1515 (w), 1450 (st), 1390 (m), 1375 (sh), 1320 (w), 1300 (m), 1230 (st), 1160 (m), 1120 (w), 1090 (m), 1010 (w), 930 (w) and 835 (m) cm$^{-1}$.

$^1$H NMR spectrum (CDCl$_3$+CD$_3$OD): δ 6.25–5.73 (c with singlet at 5.90; 2H); 5.30–4.90 (c; 2H); 3.50–2.95 (c with triplet at 3.1; J≃7.5 Hz; 4H); 2.03–1.43 (c; 2H); 0.98 (t; J≃7 Hz; 3H).

$^{13}$C NMR spectrum (DMSO-d$_6$): δ 205.2; 163.5; 162.3; 160.2; 136.8; 113.8; 104.1; 103.7; 94.1; 45.1; 26.1; 17.9 and 13.9.

EXAMPLE 17

2-Hexahydrobenzoyl-4-(propen-2-yl)phloroglucinol (20) from phlorohexahydrobenzophenone.

IR spectrum (KBr-disc): 3360 (br, st), 2940 (m), 2860 (w), 1620 (st), 1600 (sh), 1575 (m), 1510 (w), 1450 (st) 1385 (m), 1335 (m), 1320 (w), 1295 (w), 1260 (st), 1225 (st), 1185 (w), 1155 (m), 1140 (m), 1080 (m), 1070 (w), 1050 (w), 1010 (w), 930 (w), 905 (w) and 830 (m) cm$^{-1}$.

$^1$H NMR spectrum (CDCl$_3$+CD$_3$CD): δ 6.18–5.65 (c with singlet at 5.83; 2H); 5.27–4.83 (c; 2H); 3.47–3.20 (c with strong signals at 3.38 and 3.30; 3H); 2.10–1.10 (c; 10H).

$^{13}$C NMR spectrum (DMSO-d$_6$): δ 208.6; 163.9; 162.2; 159.8; 136.8; 113.8; 104.3; 102.9; 94.3; 48.6; 29.3 (2×C); 26.1 and 25.8 (3×C).

EXAMPLE 18

2-Propionyl-4-(propen-2-yl)phloroglucinol (15) from phloropropiophenone.

IR spectrum (KBr-disc): 3420 (st), 3370 (br, st), 3080 (w), 2990 (w), 2950 (w), 2930 (w), 1645 (sh), 1630 (st), 1620 (m), 1600 (m), 1580 (w), 1565 (w), 1555 (w), 1520 (w), 1505 (w), 1455 (st), 1410 (w), 1380 (w), 1365 (m), 1295 (w), 1245 (st), 1150 (m), 1130 (w), 1090 (sh), 1080 (m), 1035 (w), 1000 (w), 990 (w), 920 (m) and 830 (m) cm$^{-1}$.

$^{13}$C NMR spectrum (DMSO-d$_6$): δ 205.8; 163.4; 162.2; 160.2; 136.8; 113.8; 104.1; 103.5; 94.1; 36.4; 26.1 and 8.8.

EXAMPLE 19

2-Valeryl-4-(propen-2-yl)phloroglucinol (17) from phlorovalerophenone.

IR spectrum (KBr-disc): 3450 (st), 3400 (br, sh), 3160 (br, w), 2970 (w), 2940 (w), 2880 (w), 1655 (sh), 1645 (sh), 1640 (st), 1630 (st), 1620 (st), 1610 (st), 1570 (m), 1510 (w), 1500 (w), 1465 (sh), 1455 (st), 1435 (sh), 1390 (w), 1360 (w), 1330 (m), 1305 (m), 1290 (m), 1280 (m), 1235 (st), 1215 (sh), 1200 (sh), 1160 (m), 1135 (m), 1080 (st), 1060 (sh), 930 (m), 875 (br, w) and 825 (m) cm$^{-1}$.

$^{13}$C NMR spectrum (DMSO-d$_6$): δ 205.4; 163.5; 162.3; 160.2; 136.8; 113.8; 104.1; 103.6; 94.1; 42.8; 26.8; 26.1; 22.1 and 13.8.

EXAMPLE 20

2-Caproyl-4-(propen-2-yl)phloroglucinol (18) from phlorocaprophenone.

IR spectrum (KBr-disc): 3430 (st), 3320 (br, m), 2960 (m), 2930 (w), 2870 (w), 1635 (st), 1625 (st), 1600 (m), 1580 (m), 1560 (m), 1525 (w), 1510 (w), 1445 (st), 1400 (w), 1380 (w), 1360 (w), 1330 (w), 1300 (br, w), 1275 (m), 1265 (sh), 1250 (w), 1230 (st), 1215 (sh), 1155 (m), 1120 (w), 1090 (m), 1010 (br,w), 925 (w) and 830 (m) cm$^{-1}$.

$^{13}$C NMR spectrum (DMSO-d$_6$): δ 205.4; 163.5; 162.3; 160.2; 136.8; 113.7; 104.1; 103.6; 94.2; 43.1; 31.2; 26.1; 24.3; 21.3 and 13.8.

EXAMPLE 21

2-(4-chlorophenyl)acetyl-4-(propen-2-yl)phloroglucinol (23) from phloro-(4-chlorophenyl)acetophenone.

IR spectrum (KBr-disc): 3420 (st), 3330 (br, m), 1655 (sh), 1640 (st), 1630 (st), 1610 (st), 1565 (m), 1530 (w), 1515 (w), 1500 (w), 1465 (sh), 1450 (m), 1405 (m), 1355 (m), 1290 (br, w), 1260 (sh), 1245 (st), 1210 (m), 1160 (m), 1130 (w), 1110 (m), 1090 (m), 1035 (m), 1010 (br, w), 935 (w), 885 (w), 835 (sh), 825 (w) and 800 (w) cm$^{-1}$.

$^{13}$C NMR spectrum (DMSO-d$_6$): δ 201.8; 163.6; 162.8; 160.2; 136.6; 135.1; 131.5 (2×C); 131.0; 127.9 (2×C); 113.8; 104.2; 103.5; 94.2; 48.3 and 26.0.

EXAMPLE 22

2-(3-Ethoxy)propionyl-4-(buten-2-yl)phloroglucinol (22) from phlor-(3-ethoxy)propiophenone.

IR spectrum (KBr-disc): 3370 (br, st), 3200 (br, w), 2990 (w), 2940 (w), 2900 (w), 1665 (sh), 1650 (st), 1640 (st), 1620 (st), 1600 (sh), 1540 (w), 1460 (st), 1455 (sh), 1400 (w), 1380 (w), 1350 (w), 1310 (br, w), 1250 (st), 1160 (m), 1130 (m), 1110 (m), 1080 (m), 1030 (m), 1010 (w), 940 (w), 925 (br, w), 900 (w) and 835 (w) cm$^{-1}$.

Mass spectrum: m/e 266, 227, 222, 207 (100%), 193, 191, 165 and 164.

EXAMPLES 23 TO 26

The compounds described in Examples 23 to 26 were prepared and purified according to the procedure described in Example 2 by reacting the appropriate phlorophenone with slightly more than one molar equivalent benzyl chloride instead of prenyl chloride.

EXAMPLE 23

2-Isocaproyl-4-benzylphloroglucinol (25) from phlorisocaprophenone.

IR spectrum (KBr-disc): 3450 (st), 3270 (br, st), 3030 (w), 2980 (m), 2960 (w), 2880 (w), 1620 (st), 1570 (m), 1520 (w), 1500 (w), 1445 (st), 1400 (w), 1375 (w), 1340 (w), 1290 (w), 1270 (w), 1230 (st), 1155 (m), 1130 (m), 1090 (m), 1040 (w), 940 (w), 915 (w), 830 (m) and 715 (m) cm$^{-1}$.

$^1$H NMR spectrum (CDCl$_3$+CD$_3$OD): δ 7.25–6.95 (c with sharp signal at 7.12; 5H); 5.74 (s; 1H); 3.85 (s: 2H); 3.02 (t; J≈7.5 Hz; 2H); 1.75–1.35 (c; 3H) and 0.89 (d; J=5 Hz; 6H).

$^{13}$C NMR spectrum (DMSO-d$_6$): δ 205.7; 163.7; 162.4; 160.2; 141.8; 128.2 (2×C); 127.8 (2×C); 125.2; 105.7; 103.6; 94.2; 41.2; 33.7; 27.5 (2×C) and 22.3 (2×C).

EXAMPLE 24

2-Nonanoyl-4-benzylphloroglucinol (27) from phlorononaphenone.

IR spectrum (KBr-disc): 3420 (br, st), 2930 (m), 2860 (w), 1615 (st), 1600 (sh), 1570 (m), 1515 (w), 1500 (w), 1490 (w), 1460 (w), 1430 (st), 1385 (w), 1310 (w), 1270 (m), 1240 (m), 1200 (m), 1150 (m), 1125 (w), 1075 (m), 1045 (w), 825 (w), 735 (m), 700 (w) and 650 (w) cm$^{-1}$.

$^1$H NMR spectrum (CDCl$_3$+CD$_3$OD): δ 7.33–6.98 (c; 5H); 5.79 (s; 1H); 3.87 (s; 2H); 3.05 (t, J≈7.5 Hz; 2H); 1.80–1.10 (c with strong signal at 1.28; 12H) and 1.03–0.73 (c with strong signal at 0.87; 3H).

$^{13}$C NMR spectrum (DMSO-d$_6$): δ 205.4; 163.6; 162.4; 160.3; 141.8; 128.2 (2×C); 127.8 (2×C); 125.2; 105.7; 103.6; 94.2; 43.1; 31.2; 28.9 (2×C); 28.6; 27.5; 24.5; 22.0 and 13.9.

EXAMPLE 25

2-Butyryl-4-benzylphloroglucinol (24) from phlorobutyrophenone.

IR spectrum (KBr-disc): 3420 (br, st), 3400 (br, st), 2970 (w), 2940 (w), 2890 (w), 1610 (st), 1575 (m), 1520 (w), 1510 (w), 1450 (st), 1390 (m), 1370 (m), 1315 (m), 1245 (sh), 1220 (st), 1150 (m), 1115 (m), 1085 (m), 830 (m), 740 (m), 710 (m) and 695 (m) cm$^{-1}$.

$^1$H NMR spectrum (CDCl$_3$+CD$_3$OD): δ 7.38–7.05 (c; 5H); 5.83 (s; 1H); 3.92 (s; 2H); 3.05 (t; J≃7.5 Hz; 2H); 1.88–1.38 (c; 2H) and 0.95 (t; J≃7 Hz; 3H).

$^{13}$C NMR spectrum (DMSO-d$_6$): δ 205.2; 163.6; 162.4; 160.3; 141.8; 128.2 (2×C); 127.8 (2×C); 125.2; 105.7; 103.7; 94.2; 45.1; 27.5; 17.8 and 13.8.

EXAMPLE 26

2-Hexahydrobenzoyl-4-benzylphloroglucinol (26)

from phlorohexahydrobenzophenone.

IR spectrum (KBr-disc): 3350 (br, m), 2940 (m), 2870 (w), 1640 (st), 1620 (sh), 1590 (m), 1530 (w), 1505 (w), 1460 (m), 1450 (sh), 1390 (w), 1350 (w), 1280 (m), 1245 (m), 1165 (w), 1150 (w), 1100 (m), 1085 (sh), 850 (w), 750 (w), 720 (w) and 700 (w) cm$^{-1}$.

$^1$H NMR spectrum (CDCl$_3$+CD$_3$OD): δ 7.36–7.00 (c; 5H); 5.76 (s; 1H); 3.90 (s; 2H); about 3.80–3.33 (c; 1H) and 2.13–1.06 (c; 10H).

$^{13}$C NMR spectrum (DMSO-d$_6$): δ 208.6; 164.1; 162.3; 159.9; 141.7; 128.2 (2×C); 127.8 (2×C); 125.1; 105.9; 102.9; 94.3; 48.5; 29.2 (2×C); 27.5 and 25.7 (3×C).

EXAMPLE 27

To a mixture of anhydrous phloroglucinol (12.6 g) and aluminium chloride (48 g) in carbon disulfide (60 ml) was added nitrobenzene (45 ml) slowly over a period of 30 minutes. The latter mixture was then heated to reflux, whereupon cyclohexane carbonyl chloride (14.5 ml) in nitrobenzene (5 ml) was added over a period of 30 minutes. The reaction mixture was then refluxed for 3 hours, cooled and poured into ice water (500 ml). The resulting mixture was then subjected to steam distillation until all the nitrobenzene was removed. The residual solution was then cooled and the precipitated light yellow phlorohexahydrobenzophenone was collected and washed with water. Recrystallization from benzene afforded off-white crystals of phlorohexahydrobenzophenone, m.p. 100°–113° C.

EXAMPLE 28 p-Bromobenzoyl chloride (1.0 g) was added to a suspension of 2-isocaproyl-4-(3-methylbuten-2-yl)phloroglucinol (7) in dry benzene (25 ml) and the mixture was heated under reflux for 2 hours and evaporated to dryness. The residue was chromatographed on silica gel, as described earlier (Example 2), whereupon 2-isocaproyl-4-(3-methylbuten-2-yl)phloroglucinol-1,5-(O)-bis-(4-bromobenzoate) (28) was obtained. This was recrystallized from benzene/ethanol.

IR spectrum: 2970 (m), 2940 (w), 2880 (w), 1745 (st), 1630 (m), 1590 (st), 1485 (w), 1410 (sh), 1400 (m), 1260 (st), 1170 (m), 1095 (br, st), 1070 (st), 1010 (m), 905 (w), 880 (w) and 840 (m) cm$^{-1}$.

$^1$H NMR spectrum (CDCl$_3$): δ 13.28 (s; 1H); 8.00 (dd; J≃9 and 2 Hz; 4H); 7.63 (dd, J≃9 and 2 Hz; 4H); 6.60 (s; 1H); 5.13 (br, t; J≃7 Hz; 1H); 3.35 (d; J≃7 Hz; 2H); 2.87 (t; J≃7 Hz; 2H); 1.80–1.00 (c; with sharp signal at 1.60; 9H) and 0.72 (d; J≃6 Hz; 6H).

X-ray crystallographic data obtained for 28, with reference to the accompanying sketch:

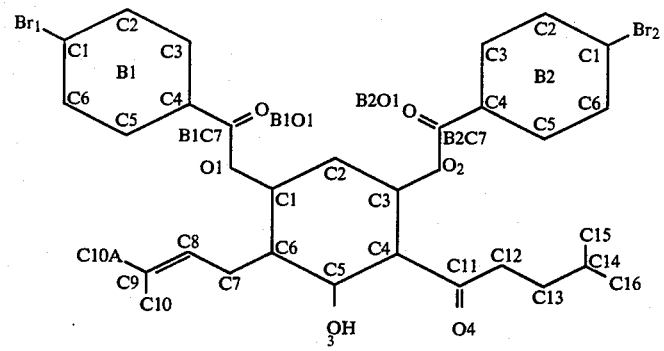

TABLE 2

| ATOM | FRACTIONAL COORDINATES | | | THERMAL PARAMETERS |
| --- | --- | --- | --- | --- |
| | X/A | Y/B | Z/C | U |
| Br 1 | .0817 | .3629 | .0296 | .0624 |
| B1O1 | .2272 | .2442 | .2991 | .0534 |
| B1C1 | .1294 | .3449 | .0999 | .0650 |
| B1C2 | .1206 | .2853 | .1402 | .0525 |
| B1C3 | .1554 | .2681 | .1932 | .0511 |
| B1C4 | .1988 | .3105 | .2051 | .0368 |
| B1C5 | .2100 | .3764 | .1639 | .0459 |
| B1C6 | .1736 | .3928 | .1095 | .0456 |
| B1C7 | .2339 | .2878 | .2612 | .0544 |
| C1 | .3161 | .3247 | .3199 | .0438 |
| C2 | .3131 | .3845 | .3663 | .0319 |
| C3 | .3541 | .3848 | .4129 | .0480 |
| C4 | .3936 | .3315 | .4173 | .0348 |
| C5 | .3945 | .2753 | .3692 | .0417 |
| C6 | .3546 | .2691 | .3188 | .0311 |
| C7 | .3548 | .2062 | .2675 | .0420 |
| C8 | .3590 | .3706 | .2346 | .0529 |
| C9 | .3905 | .3984 | .2182 | .0761 |
| C10 | .4291 | .2779 | .2323 | .1158 |
| C10A | .3840 | .5805 | .1866 | .1103 |
| C11 | .4368 | .3250 | .4692 | .0346 |
| C12 | .4367 | .3385 | .5230 | .0515 |
| C13 | .4846 | .2785 | .5707 | .0664 |
| C14 | .4779 | .2759 | .6236 | .1019 |
| C15 | .4511 | .1047 | .6244 | .1555 |
| C16 | .5213 | .2207 | .6723 | .1672 |
| O1 | .2773 | .3290 | .2682 | .0450 |
| O2 | .3506 | .4713 | .4580 | .0423 |
| O3 | .4338 | .2273 | .3687 | .0559 |
| O4 | .4729 | .2940 | .4677 | .0612 |
| B2C1 | .3023 | .7767 | .5795 | .0549 |
| B2C2 | .2828 | .6046 | .5711 | .0678 |
| B2C3 | .2920 | .4692 | .5407 | .0547 |
| B2C4 | .3184 | .5232 | .5151 | .0420 |
| B2C5 | .3370 | .7039 | .5221 | .0752 |
| B2C6 | .3290 | .8308 | .5565 | .0654 |
| B2C7 | .3266 | .3949 | .4792 | .0430 |
| B2O1 | .3119 | .2391 | .4705 | .0634 |
| Br2 | .2907 | .9488 | .6223 | .0738 |

EXAMPLE 29

A stirred mixture of 2-isocaproyl-4-(3-methylbuten-2-yl)=phloroglucinol (7) (1 g) and anhydrous potassium carbonate (1 g) in dry acetone (50 ml) was heated to reflux and dimethyl sulphate (2 ml) was added dropwise. After completion of the addition the mixture was heated under reflux for a further period of 4 hours, cooled to room temperature and filtered. The filtrate was evaporated to dryness under vacuum. The residue was stirred overnight with aqueous sodium hydroxide (5%, 50 ml) and extracted with ether. The ether extract was washed with water, dried over sodium sulphate and evaporated to dryness. The residue was chromatographed on silica gel, as described earlier (Example 2), whereupon 2-isocaproyl-4-(3-methylbuten-2-yl)phloroglucinol-1,5-(O)-dimethylether (29), which melted at 86°–88° C. after recrystallization from benzene/petroleum ether, was obtained.

IR spectrum: 3010 (w), 2970 (m), 2940 (br, m), 2880 (m), 2860 (sh), 1615 (st), 1590 (st), 1465 (br, m), 1430 (m), 1410 (m), 1380 (m), 1325 (w), 1275 (m), 1220 (st), 1210 (st), 1200 (sh), 1170 (m), 1140 (m), 1120 (st), 875 (m), 795 (w), 785 (m) and 770 (w) cm$^{-1}$.

$^1$H NMR spectrum (CDCl$_3$): δ 13.73 (s; 1H); 5.90 (s; 1H); 5.15 (br t; J≃7 Hz; 1H); 3.83 (s; 6H); 3.33–2.77 (c; 4H); 2.00–1.20 (c; two sharp signals at 1.75 and 1.63; 9H) and 0.92 (d; J≃5 Hz; 6H).

EXAMPLE 30

2-Isocaproyl-4-(3-methylbuten-2-yl)phloroglucinol (7) (2 g) was suspended in benzene (25 ml), Trifluoro acetic acid (1.5 ml) was added and the mixture was stirred for 6 hours at room temperature. The resulting solution was stripped to dryness under vacuum. The residue was chromatographed, preferably on silica gel (open column chromatography, preparative HPLC or preparative TLC) using preferably mixtures of benzene and ethyl acetate or petroleum ether and ethyl acetate for elution. Two chromanes, namely 5,7-dihydroxy-2,2-dimethyl-8-isocaproyl chroman (31) and 5,7-dihydroxy-2,2-dimethyl-6-isocaproyl chroman (33), were obtained in a ratio of about 3 to 2. These chromanes were both recrystallized from petroleum ether to give light straw coloured crystals.

Chroman (31) with longest column retention time (benzene: ethyl acetate; 9:1):

IR spectrum (KBr-disc): 3300 (br, m), 2960 (sh), 2940 (m), 2920 (m), 2860 (w), 1610 (st), 1595 (st), 1500 (m), 1415 (st), 1370 (w); 1350 (m), 1340 (m), 1270 (m); 1250 (m), 1230 (m), 1155 (st), 1115 (sh), 1105 (st), 1080 (m), 1030 (w), 1015 (w), 945 (w), 930 (w), 885 (w) and 830 (m) cm$^{-1}$.

$^1$H NMR spectrum (CDCl$_3$): δ 13.90 (s; 1H); 5.93 (s; 1H); 3.03 (t; J≃7.5 Hz; 2H); 2.57 (t; J≃7 Hz; 2H); 2.0–1.5 (c, with prominent signals at δ 1.87; 1.77 and 1.67; 5H); 1.37 (s, 6H) and 0.93 (d; J≃5 Hz; 6H).

Chroman (33) with shortest column retention time (benzene: ethyl acetate; 9:1):

IR spectrum (KBr-disc): 3400 (sh), 3340 (m), 2970 (m), 2950 (m), 2890 (w), 1625 (st), 1610 (st), 1515 (w), 1475 (w), 1465 (w), 1455 (w), 1435 (m), 1400 (m), 1385 (m), 1330 (m), 1315 (m), 1290 (m), 1270 (m), 1210 (w), 1170 (m), 1125 (st), 1100 (m), 940 (w), 910 (w), 895 (m), 875 (w), 835 (w), 820 (m) and 720 (w) cm$^{-1}$.

$^1$H NMR spectrum (CDCl$_3$): δ13.48 (s; 1H); 5.77 (s; 1H); 3.07 (t; J≃7.5 Hz; 2H); 2.58 (t, J≃7 Hz; 2H); 2.12–1.43 (c; with prominent signals at δ1.87; 1.77 and 1.66; 5H); 1.30 (s, 6H) and 0.91 (d; J≃5 Hz; 6H).

EXAMPLE 31

Following the procedure outlined in Example 30, the reaction of 3-prenyl phlorononaphenone (10) with trifluoro acetic acid gave rise to 2 chromanes, namely 5,7-dihydroxy-2,2-dimethyl-8-nonanoyl chroman (32) and 5,7-dihydroxy-2,2-dimethyl-6-nonanoyl chroman (34), in a ratio of about 3 to 2.

Chroman (32) with longest column retention time (benzene:ethyl acetate; 9:1):

IR spectrum (KBr-disc): 3200 (br, m), 2940 (m), 2910 (st), 2840 (m), 1600 (st), 1595 (sh), 1545 (w), 1485 (w), 1400 (w), 1360 (w), 1345 (w), 1325 (m), 1270 (m), 1245 (st), 1225 (m), 1210 (sh), 1155 (m), 1145 (m), 1115 (m), 1105 (st), 1075 (m), 880 (w) and 845 (w).

$^{13}$C NMR spectrum (CDCl$_3$+CD$_3$OD): δ206.8; 164.9; 160.9; 157.4; 106.0; 100.0; 95.5; 76.1; 44.6; 31.9; 31.6; 29.7; 29.6; 29.3; 26.8 (2×C); 25.4; 22.7; 16.4 and 14.1.

Chroman (34) with shortest column retention time (benzene:ethyl acetate; 9:1):

IR spectrum (KBr-disc): 3300 (br, m), 2990 (m), 2930 (st), 2870 (m), 1630 (st), 1595 (st), 1505 (w), 1470 (w), 1460 (w), 1435 (m), 1395 (m), 1340 (w), 1280 (m), 1240 (m), 1165 (st), 1130 (m), 1095 (m), 1085 (m), 1060 (w), 980 (w), 935 (w), 900 (m), 845 (m), 760 (w), 745 (w) and 730 (m) cm$^{-1}$.

$^{13}$C NMR spectrum (CDCl$_3$+CD$_3$OD): δ206.9; 163.9; 160.6; 159.0; 104.5; 101.2; 95.5; 75.9; 44.0; 32.3; 32.0; 29.7; 29.6; 29.3; 26.7 (2×C); 25.3; 22.7; 16.2 and 14.1.

EXAMPLE 32

Following the procedure outlined in Example 30, the reaction of 2-butyryl-4-(3-methylbuten-2-yl)phloroglucinol (3) with trifluoro acetic acid gave rise to two chromanes, of which the chromane with the longest column retention time (silica gel, benzene:ethyl acetate; 9:1), 5,7-dihydroxy-2,2-dimethyl-8-butyryl chroman (30), was isolated.

IR spectrum (KBr-disc): 3300 (br, m), 2970 (m), 2940 (m), 2880 (w), 1620 (st), 1600 (st), 1580 (sh), 1520 (m), 1500 (w), 1460 (w), 1425 (m), 1390 (sh), 1380 (m), 1340 (w), 1320 (w), 1295 (w), 1270 (w), 1255 (m), 1230 (br, m), 1170 (m), 1155 (m), 1130 (m), 1120 (m), 1090 (m), 1040 (w), 1020 (w), 960 (w), 945 (w), 910 (w), 895 (w) and 830 (m) cm$^{-1}$.

$^{13}$C NMR spectrum (DMSO-d$_6$): δ205.0; 164.2; 162.4; 156.6; 104.5; 99.8; 94.6; 75.7; 45.7; 31.0; 26.3 (2×C); 18.3; 16.2 and 13.8.

EXAMPLE 33

Phloroglucinol (12.6 g) was reacted with allyl chloride (7.6 g) according to the procedure outlined in Example 2. The crude reaction product, containing 2-allyl phloroglucinol, and aluminium chloride (48 g) were dissolved in carbon disulfide (60 ml). To this solution, well-stirred, was added nitrobenzene (45 ml) over a period of 30 minutes. A solution of butyryl chloride (12.7 g) in nitrobenzene (5 ml) was then added over a period of 20 minutes to the latter mixture. The reaction mixture was refluxed for 4 hours, then cooled to room temperature and finally poured into ice-cold diluted hydrochloric acid (prepared from 20 ml concentrated hydrochloric acid and 500 ml water). The latter mixture was extracted three times with ether. The ether extracts were combined and dried over sodium sulphate and then stripped to dryness under vacuum to yield a light yellow oil. The oil was chromatographed over silica gel (petroleum ether:ethyl acetate; 4:1).

Two dihydrobenzofuran compounds were isolated:

The compound with shortest column retention time, 4,6-dihydroxy-5,7-dibutyryl-2-methyl-2,3-dihydrobenzofuran (37):

IR spectrum (KBr-disc): 2980 (sh), 2960 (m), 2930 (w), 2870 (w), 1650 (st), 1640 (st), 1600 (m), 1490 (w), 1470 (w), 1460 (w), 1440 (m), 1405 (w), 1390 (w), 1355 (w), 1330 (w), 1310 (w), 1290 (w), 1270 (w), 1240 (br, w), 1215 (m), 1170 (m), 1120 (w), 1100 (w), 1065 (w), 1040 (w), 950 (br, w), 930 (br, m), 825 (w), 805 (w), 790 (w) and 770 (w) cm$^{-1}$.

$^{13}$C NMR spectrum (DMSO-d$_6$): δ206.3; 204.8; 170.6; 166.5; 166.1; 104.5; 104.1; 100.0; 83.5; 45.7; 44.3; 32.1; 21.8; 17.8; 17.5 and 13.8 (2×C).

The compound (35) with longest column retention time, either 7-butyryl-4,6-dihydroxy-2-methyl-2,3-dihydrobenzofuran or 5-butyryl-4,6-dihydroxy-2-methyl-2,3-dihydrobenzofuran:

IR spectrum (KBr-disc): 3200 (br, m), 2960 (m), 2930 (w), 2870 (w), 1645 (st), 1615 (w), 1580 (m), 1570 (m), 1550 (w), 1530 (w), 1520 (w), 1505 (w), 1490 (w), 1470 (sh), 1460 (m), 1450 (sh), 1440 (w), 1420 (w), 1395 (w), 1360 (br, w), 1335 (br, w), 1290 (st), 1270 (w), 1250 (m), 1225 (m), 1175 (st), 1120 (m), 1085 (m), 1060 (m), 1015 (w) and 835 (m) cm$^{-1}$.

$^{13}$C NMR spectrum (DMSO-d$_6$): δ203.6; 164.5; 162.5; 160.6; 103.9; 100.7; 95.4; 81.7; 43.8; 32.8; 21.6; 17.7 and 13.7.

EXAMPLE 34

2,4-Dibutyrylphloroglucinol (1)

METHOD 1

A solution of phorbutyrophenone (4.9 g) in anhydrous (vacuum-distilled) methanesulphonic acid (10 ml) was added concomitantly (under a nitrogen atmosphere) with 1.8 g acrylic acid to a stirring solution of phosphorous pentoxide (2 g) in 40 ml methanesulphonic acid at 70° C. The reaction mixture was stirred for a further 30 minutes at 70° C., cooled to room temperature and poured into an ice/water mixture. This solution was extracted with ether (3×150 ml). The combined extracts were washed with water, sodium bicarbonate solution and dried over sodium sulphate. Evaporation of the ether afforded an oily product which was chromatographed (silica gel, petroleum ether:ethyl acetate, 4:1) to yield 2,4-dibutyrylphloroglucinol (1) as the first product to eluate. The solution was stripped to dryness and the product recrystallized from benzene to yield 1 as colourless needles.

METHOD 2

To a solution of phlorbutyrophenone (4.9 g) and aluminium chloride (15 g) in carbon disulphide (20 ml), nitrobenzene (15 ml) was added over a period of 30 minutes under heavy stirring. The reaction mixture was heated to 46° C. whereafter a mixture of butyrylchloride (8 ml) and nitrobenzene (5 ml) was added dropwise over a period of 30 minutes. The reaction mixture was boiled for a further 2 hours and poured into ice cold water (500 ml) containing 20 ml concentrated HCl. Nitrobenzene was removed by means of steam distillation and the mixture was allowed to stand overnight. The crystals were filtered, washed with petroleum ether and chromatographed (silica gel, petroleum ether:ethyl acetate, 4:1) to yield pure 2,4-dibutyrylphloroglucinol (1) upon evaporation of the solvent.

IR spectrum (KBr-disc): 3180 (br, m), 2980 (m), 2940 (w), 2890 (w), 1635 (sh), 1625 (st), 1600 (sh), 1560 (m), 1450 (br, w), 1425 (m), 1400 (sh), 1385 (m), 1335 (br, w), 1275 (m), 1210 (st), 1135 (w), 1120 (w), 1050 (w), 1015 (w), 990 (br, w), 910 (w), 860 (br, w) and 835 (m) cm$^{-1}$.

$^{13}$C NMR spectrum (DMSO-d$_6$): δ205.9 (2×C); 170.9; 168.2 (2×C); 103.5 (2×C); 94.8; 45.3 (2×C); 17.5 (2×C) and 13.7 (2×C).

EXAMPLE 35

2-Butyryl-4-(propen-2-yl)phloroglucinol (16) was treated by the same procedure as described for the preparation of 2,4-dibutyrylphloroglucinol in Example 34 (Method 2) to yield 2,4-dibutyryl-6-(propen-2-yl)phloroglucinol (21) after chromatography on silica gel (petroleum ether, ethyl acetate, 4:1).

IR spectrum (KBr-disc): 2980 (sh), 2960 (st), 2940 (m), 2870 (m), 2600 (br, w), 1650 (st), 1635 (st), 1600 (st), 1570 (sh), 1555 (w), 1490 (w), 1470 (m), 1460 (m), 1440 (st), 1405 (m), 1390 (m), 1355 (m), 1330 (w), 1310 (w), 1285 (w), 1270 (w), 1240 (w), 1215 (st), 1170 (st), 1130 (w), 1120 (m), 1100 (w), 1070 (w), 1040 (w), 955 (w), 925 (br, st), 825 (w), 805 (w), 790 (w), 770 (w) and 700 (w) cm$^{-1}$.

Mass spectrum: m/e 306 (M+), 291, 263 (100%), 245, 193 and 43.

EXAMPLE 36

5,7-Dihydroxy-6,8-dibutyryl-2,2-dimethylchroman (36).

Phloroglucinol was treated with prenylchloride using the same procedure as described in Example 2 to yield prenylphloroglucinol. Prenylphloroglucinol was treated with butyrylchloride, according to the same procedure as described for the preparation of 2,4-dibutyrylphloroglucinol in Example 34 (Method 2) to yield 5,7-dihydroxy-6,8-dibutyryl-2,2-dimethylchroman (36) after chromatography with silica gel (petroleum ether, ethyl acetate, 4:1).

IR spectrum (KBr-disc): 2960 (m), 2930 (m), 2870 (m), 1625 (br, st), 1570 (w), 1555 (w), 1470 (w), 1460 (w), 1450 (w), 1430 (w), 1385 (br, w), 1300 (br, w), 1275 (w), 1200 (m), 1170 (m), 1130 (m), 1070 (br, w), 960 (w), 950 (w), 930 (w), 900 (w) and 800 (br, w) cm$^{-1}$.

Mass spectrum: m/e 334 (M+), 289 (100%), 279, 201, 121, 69 and 43.

ANTIBACTERIAL/ANTIFUNGAL PROPERTIES AND RESULTS

For testing against the bacteria, concentrations of each of the compounds were prepared in Brain Heart Infusion broth (Oxoid CM225) in two-fold steps from 1000 μg/ml to 1 μg/ml. Solutions containing 1000 μg/ml were prepared by dissolving 20 mg of each compound in 5 ml of acetone and this was then made up to 20 ml with Brain Heart Infusion Broth. Serial two-fold dilutions were then prepared in the broth down to 1 μg/ml.

For testing against the fungi, concentrations of each of the compounds were prepared in Sabouraud liquid medium in two-fold steps from 100 μg/ml to 0.1 μg/l. 500 μg/ml solutions were prepared by dissolving 10 mg in 5 ml of acetone, made up to 20 ml with Sabouraud liquid medium. 4 ml of the 500 μg/ml concentration was then made up to 20 ml with Sabouraud liquid medium to give a concentration of 100 μg/ml. Serial two-fold dilutions were prepared from this in the same medium down to 0.1 μg/ml.

For testing against the bacteria each of the prepared test concentrations and acetone controls prepared in Brain Heart Infusion were dispensed in 2 ml amounts for each organism. A growth control of 2 ml of Brain Heart Infusion was included in each series.

For the fungi the same procedure was followed using the concentrations made up in Sabouraud liquid medium. The Nystatin concentrations were also dispensed in 2 ml amounts for each organism. Growth controls of Sabouraud liquid medium were included in each series.

To each of the prepared sets of concentrations of each compound were added 0.1 ml aliquots of the organism suspensions prepared as described previously. All the bottles were incubated at 37° C. for 48 hours in the case of the bacteria and from 5 to 15 days for the fungi (until growth controls had grown in each case).

After incubation the broths were examined for evidence of growth. The lowest concentration of the test compound which prevented growth was recorded as the Minimum Inhibitory Concentration (MIC).

Sub-cultures were made from all the broths showing no growth and from the growth controls. The sub-cultures were made onto Brain Heart Infusion Agar (Oxoid CM375) for the bacteria and onto Sabouraud Dextrose Agar (Oxoid CM41) for the fungi. The plates were incubated at 37° C. for 48 hours for bacteria and 5 to 14 days for fungi.

After incubation the plates were examined for growth. The lowest concentration showing no evidence of growth was recorded as the Minimal Microbiocidal Concentration (MMC).

The antibacterial/antifungal activities of a number of representative compounds are illustrated by the examples given in the accompanying table.

ACUTE TOXICITY DATA

Male and female CD-1 mice were fasted for 18 hours prior to the experiment, but water was available ad libitum except during the observation period. The test compounds were prepared in 1% tragacanth and were administered orally to groups of two male and two female mice.

All compounds were tested at dose levels of 1000, 464, 215 and 100 mg/kg. Immediately after dosing, the mice were replaced in their "home" cage and were observed daily for 7 days post dose and any mortalities recorded.

The acute toxicities, as determined by the above procedure, of a number of representative compounds are given in the accompanying table.

TABLE 3

$LD_{50}$ VALUES AND ANTIMICROBIC ACTIVITIES (MIC VALUES IN $\mu g/ml$)

| COMPOUND NUMBER | S. AUREUS | St. PYOGENES | C. ALBICANS | Tr. MENTAGRO-PHYTES | Tr. RUBRUM | Sp. SCHENKII | Mic. CANIS | $LD_{50}$ |
|---|---|---|---|---|---|---|---|---|
| 1 | 2 | 1 | 13 | 6 | 6 | 6 | 3 | >1000 |
| 2 | 125 | 8 | 50 | 25 | 13 | 25 | 13 | >1000 |
| 4 | 64 | 16 | 25 | 13 | 13 | 25 | 13 | >1000 |
| 5 | 8 | 4 | 13 | 6 | 3 | 13 | 1,6 | >1000 |
| 6 | 250 | 8 | >100 | 100 | 25 | 50 | 50 | >1000 |
| 7 | 16 | 8 | 25 | 6 | 6 | 25 | 6 | 1000 |
| 8 | 32 | 8 | 13 | 6 | 6 | 13 | 6 | >1000 |
| 9 | 32 | 8 | 6,2 | 6,2 | 3,1 | 6,2 | 1,6 | <100 |
| 11 | 64 | 2 | 100 | 100 | 50 | >100 | 50 | 597 |
| 14 | 16 | 8 | 100 | 100 | >100 | 100 | 50 | 1000 |
| 15 | 250 | 125 | 100 | 25 | 50 | 50 | 50 | >1000 |
| 17 | 64 | 16 | 25 | 13 | 13 | 25 | 6 | >1000 |
| 18 | 16 | 8 | 13 | 6 | 13 | 13 | 6 | >1000 |
| 19 | 16 | 4 | 25 | 13 | 6 | 13 | 6 | >1000 |
| 20 | 32 | 8 | 25 | 13 | 25 | 25 | 13 | >1000 |
| 23 | 32 | 8 | 13 | 13 | 13 | 25 | 6 | >1000 |
| 24 | 16 | 8 | 25 | 13 | 6 | 25 | 13 | 1000 |
| 25 | 16 | 8 | 13 | 3 | 6 | 25 | 6 | 1000 |
| 27 | 2 | 1 | 100 | 5 | >100 | 50 | 50 | >1000 |
| 30 | 32 | 32 | 25 | 13 | 13 | 25 | 6 | >1000 |
| 31 | 16 | 8 | 100 | 6 | 25 | 6 | 13 | >1000 |
| 32 | 64 | <1 | 100 | >100 | >100 | 100 | 100 | >1000 |
| 33 | 125 | 64 | 100 | >100 | 25 | >100 | 100 | >1000 |
| 34 | 500 | 4 | 100 | >100 | 100 | >100 | >100 | >1000 |
| 35 | 125 | 32 | 25 | 25 | 25 | 50 | 12,5 | >1000 |
| 36 | 250 | 64 | 100 | 100 | 100 | 100 | 100 | >1000 |
| 37 | 125 | 32 | >100 | >100 | 100 | >100 | >100 | >215 |

As can be seen from the aforegoing, these compounds generally exhibit useful in vitro antibacterial and antimycotic activity, and in particular very low oral acute toxicity. Antibacterial activity of these compounds is directed particularly against Gram-positive bacteria for example *Staphylococcus aureus*. Consequently the physiologically acceptable compounds of the invention may enjoy useful applications in the medical and veterinary fields.

These compounds have also shown useful antimycotic activity, in respect of which they may likewise be employed both in the medical and in the veterinary fields, for example for treating local and systemic mycotic infections for example mycotic infections in or on the skin or under nails, in the lungs, upper airways, eyes, hair, for vaginal infections, or any other local or systemic mycotic infection. Likewise these compounds may have useful veterinary applications, for example for treating mastitis.

A further interesting attribute of these compounds is that there are indications that these compounds generally exhibit both antibacterial and antimycotic activity. A consequence of this dual activity is that in treatment of a bacterial or mycotic infection, these compounds are in principle capable of maintaining a balance between bacteria and fungi mycosis.

In addition to the abovementioned pharmaceutical indications, these compounds because of their activity can also be used as a preservative for food and beverages, for example for humans and animals such as livestock, in addition to a preservative for natural products.

Furthermore, such compounds can be used as a general disinfectant, for example in hospitals, storerooms, dairies, or for spraying or washing any area requiring to be disinfected. In this regard, these compounds can also be used in soaps, detergents, and the like.

In respect of pharmaceutical compositions, it may be mentioned that one or more of the above suitable compounds may be incorporated in a pharmaceutical composition for administration to a human or animal patient. The method of preparing such composition includes the steps of ensuring that the compound(s) are free of undesirable impurities—this may require repeated re-crystallisation, or washing; comminuting the compound(s) to a required particle size; and incorporating and providing the compounds in a desired form or administration to a patient, for example in solid (powder, tablet or capsule form), or liquid form (injectable or liquid medicine) for internal or external application, for example in a suspension or cream for topical application, or in a (dissolvable) jelly form.

Although the invention in its various aspects has been described above in certain preferred embodiments, it will be readily apparent to any person skilled in the art that various modifications and/or variations of the invention are possible. Such modifications and/or variations of the invention are to be considered as forming part of the invention and as falling within the scope of the appended claims which are also to be considered as part of the disclosure of this invention.

What is claimed is:

1. A process for preparing compounds of formula A

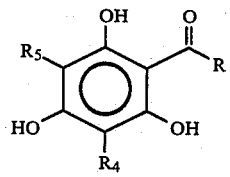

wherein
R is a branched or unbranched alkyl, cycloalkyl or aralkyl group, which group is optionally substituted by a halogen, hydroxy or alkoxy group;
$R_4$ is an alkyl, alkenyl or aralkyl group, which group optionally contains as a substituent an alkyl, aryl, aralkyl, halogen, hydroxy, or alkoxy group; and
$R_5$ is hydrogen, halogen, an alkyl, aralkyl, alkanoyl or aryl group, which group optionally contains as a substituent an alkyl, aryl, aralkyl, halogen, hydroxy or alkoxy group;
and pharmaceutically acceptable salts thereof;

which process comprises reacting a compound of formula B

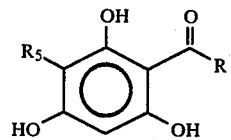

wherein R and $R_1$ are as defined above, with an appropriate organic halide being $R_4$-halide wherein $R_4$ is as defined above in the presence of a cuprous chloride catalyst and a base being a carbonate base or a like base having a similar pH range.

2. A process as claimed in claim 1, wherein said $R_4$-halide, is an organic chloride compound.

3. A process as claimed in claim 2, wherein said $R_4$-halide, is prenyl chloride, allyl chloride or benzyl chloride.

4. A process as claimed in claim 1 wherein the base is sodium carbonate.

5. A process as claimed in claim 1, wherein the process is carried out in a two phase system by dissolving or suspending a compound of formula B and the metal ion catalyst in ether or any suitable hydrophobic solvent, adding an aqueous solution of the base, and finally adding the organic halide to the well stirred two phase system.

6. A process as claimed in claim 5, wherein $R_5$ is hydrogen and R is 3-methylbutyl.

7. A process as claimed in claim 5, wherein $R_5$ is hydrogen and R is propyl.

8. A process as claimed in claim 5, wherein $R_5$ is hydrogen and R is octyl.

9. A process as claimed in claim 5, wherein $R_5$ is hydrogen and R is benzyl.

10. A process as claimed in claim 5, wherein $R_5$ is hydrogen and R is cyclohexyl.

11. A process as claimed in claim 5, wherein $R_5$ is hydrogen and R is ethyl.

12. A process as claimed in claim 5, wherein $R_5$ is hydrogen and R is butyl.

13. A process as claimed in claim 5, wherein $R_5$ is hydrogen and R is pentyl.

14. A process as claimed in claim 5, wherein $R_5$ is hydrogen and R is heptyl.

15. A process as claimed in claim 5, wherein $R_5$ is hydrogen and R is cyclopentyl.

16. A process as claimed in claim 5, wherein $R_5$ is hydrogen and R is hexyl.

17. A process as claimed in claim 5, wherein $R_5$ is hydrogen and R is p-chlorobenzyl.

18. A process as claimed in claim 5, wherein $R_5$ is hydrogen and R is (2-ethoxy)ethyl.

* * * * *

UNITED STATES PATENT AND TRADEMARK OFFICE
CERTIFICATE OF CORRECTION

PATENT NO. : 4,578,520
DATED : March 25, 1986
INVENTOR(S) : FOURIE, et al

It is certified that error appears in the above-identified patent and that said Letters Patent is hereby corrected as shown below:

On the title page,
the title is amended to read:

PROCESS FOR PREPARING PHLOROPHENONE COMPOUNDS

The abstract is amended to read:

A process for preparing phlorophenone compounds of the formula:

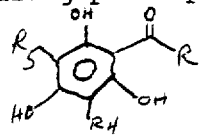

wherein R is a branched or unbranched alkyl, cycloalkyl or aralkyl group optionally substituted by halogen, hydroxy or alkoxy $R_4$ is alkyl, alkenyl or optionally substituted aralkyl, $R_5$ is hydrogen, halogen, alkyl, aralkyl, alkaryl or optionally substituted aryl or a pharmaceutically acceptable salt thereof by reaction of a 2-alkanoyl phloroglucinol with an $R_4$-halide in the presence of a catalyst and base.

Signed and Sealed this

Thirtieth Day of December, 1986

*Attest:*

DONALD J. QUIGG

*Attesting Officer*     *Commissioner of Patents and Trademarks*